United States Patent [19]

Fischer et al.

[11] 4,390,518

[45] Jun. 28, 1983

[54] METHOD FOR THE DETERMINATION OF LEUKEMIC CELLS

[75] Inventors: Wolfgang Fischer, Darmstadt; Renate Link, Reinheim, both of Fed. Rep. of Germany

[73] Assignee: Merck Patent Gesellschaft mit beschrankter Haftung, Darmstadt, Fed. Rep. of Germany

[21] Appl. No.: 254,723

[22] Filed: Apr. 16, 1981

[30] Foreign Application Priority Data

Apr. 16, 1980 [DE] Fed. Rep. of Germany ....... 3014563

[51] Int. Cl.³ .............................................. G01N 1/30
[52] U.S. Cl. .......................................... 424/3; 424/7.1
[58] Field of Search ........................ 424/3.7; 23/230 B

[56] References Cited

PUBLICATIONS

Lillie, Histopath. Tech. & Practical Histochem., McGraw Hill, N.Y., 1965, 3rd Ed., pp. 117, 125, 286, 287.

*Primary Examiner*—Anna P. Fagelson
*Attorney, Agent, or Firm*—Millen & White

[57] ABSTRACT

A method for the detection and for the differential diagnostic determination of leukemic cells, comprises treating leucocytes with a supravital dye and evaluating the different staining of healthy and leukemic cells. Preferred dyes are triphenylmethane dyes of the phthalein and sulphophthalein classes.

6 Claims, No Drawings

METHOD FOR THE DETERMINATION OF LEUKEMIC CELLS

BACKGROUND OF THE INVENTION

The present invention relates to a method for detection and differential diagnostic determination of leukemic cells by selective staining of leukemic blood cells.

The known staining methods for leucocytes are unspecific because they stain both normal and leukemic cells. For diagnosis of leukemia it has hitherto been necessary to demonstrate a pathogenic increase in the number of leucocytes by determining the number of leucocytes in the blood circulating in the vessels. Diagnosis of leukemia via the determination of changed enzymatic activities of leukemia cells is time-consuming and expensive in terms of apparatus. A staining method for leukemic cells using merocyanine dyes has been disclosed in Cell 13, 487 (1978). Evaluation is by fluorescence microscopy. This method is disadvantageous since it requires a fluorescence microscope which is considerably more expensive than a normal microscope. Thus, such instruments are not available in all locations where it could be of interest to carry out a leukemia test. A further disadvantage is that stained and unstained cells cannot be evaluated at the same microscope setting; this makes the evaluation involved.

SUMMARY OF THE INVENTION

Accordingly, it is an object of this invention to provide a simple method by which leukemic blood cells can be differentiated from normal leucocytes by specific staining.

Upon further study of the specification and appended claims, further objects and advantages of this invention will become apparent to those skilled in the art.

These objects have been atained by this invention by providing a method for the detection and for the differential diagnostic determination of leukemic cells, comprising treating leucocytes with a supravital dye and evaluating the different staining of healthy and leukemic cells.

DETAILED DISCUSSION

It has been found that the different behavior of normal leucocytes and leukemic cells towards supravital dyes can be used for a reliable leukemia diagnosis.

Preferred supravital dyes for carrying out the method of this invention include triphenymethane dyes of the phthalein and sulphophthalein category, such as eosine, erythrosine, phloxine, bromophenol blue, bromochlorophenol blue and related dyes.

Surprisingly, it has been found that staining, flawless from the standpoint of differential diagnosis, can be effected with these dyes. Usually it is not possible at all to carry out supravital staining of leucocytes with these dyes. However, it has been discovered that although the healthy cells remain unstained, the leukemic leucocytes are stained. The staining occurs very rapidly and the differences in color between healthy and diseased cells are very distinct, so that the evaluation can be carried out easily by trained personnel. With phloxine, for example, the leukemic cells are stained red, and with bromochlorophenol blue they are stained blue; the healthy cells remain colorless in both cases.

The stainings can be carried out using fully conventional procedures, i.e., using conditions under which the supravital dyes have previously been employed for staining the diverse constituents of the blood. See, e.g., Staining Procedures, 3rd. Ed., The William and Wilkins Co., 1973, p. 129, whose disclosure is incorporated by reference herein. The dye solutions should be used in a concentration of about 0.01 to 0.5%, preferably 0.05 to 0.2%, in physiological saline solution.

For carrying out the method, a dextran solution, for example, is added to EDTA-blood and the blood is left to stand in a closed tube for one hour at 37° C. The supernatant plasma is pipetted off and centrifuged and the residue is taken up in phsiological saline solution. The dye solution is then added and the whole is mixed; a portion of the mixture is applied to a microscope slide, immediately covered with a cover glass and evaluated under a microscope. In general, 0.01-10.0 ml of dye solution is added per milliliter of test sample depending on the usual factors such as leucocyte concentration, etc. Total elapsed time from addition of dye solution to the test sample to beginning of evaluation is generally 1-5 minutes.

The quantitative evaluation is carried out by determining the number of stained leucocytes (x) and the total number of leucocytes (y), in a specific field of view of the transmitted light microscope. From these figures, the percentage (A) of stained cells is calculated using the equation $$A = (x/y) \cdot 100.$$

For rapid determination of leukemic leucocytes, it is also possible to apply a few drops of the plasma to a microscope slide and to cover this with a water-soluble film which contains the requisite dyes in homogenous distribution.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE I

Analysis of blood with a reduced, normal or slightly increased number of leucocytes (up to about 40,000/μl of blood).

8 drops of dextran solution (Dextran T 500, 6% solution in 0.9% sodium chloride solution) were added to 2 ml of EDTA-blood and the mixture was left to stand in a closed tube for one hour at 37° C. The supernatant plasma was then pipetted off and centrifuged for 5 minutes at 1000-2000 rpm. The supernatant solution was poured off, 2 drops of 0.9% sodium chloride solution were added to the residue and the whole was mixed. 2 drops of a 0.1% phloxine solution in 0.85% sodium chloride solution were added to this solution and the whole was mixed again. 0.02 ml of this mixture was applied to a microscope slide, immediately covered with a cover glass and evaluated under a transmitted light microscope (magnification: 6.3×1.25×25). The healthy cells were colorless and the diseased cells were stained red.

EXAMPLE II

Analysis of blood with a greatly increased number of leucocytes (above about 40,000/μl of blood).

Analogously to Example I, 8 drops of dextran solution were added to 2 ml of EDTA-blood and the mixture was left to stand without agitation in a closed tube for one hour at 37° C. 0.02 ml of the supernatant plasma was drawn off, 2 drops of sodium chloride solution were added and the whole was mixed. 2 drops of a 0.08% solution of bromochlorophenol blue in 0.85% sodium chloride solution were added to this solution and the whole was mixed again. 0.02 ml of this mixture was applied to a microscope slide, immediately covered with a cover glass and evaluated under a transmitted light microscope. The healthy cells were colorless and the diseased cells were stained blue.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A supravital method for the detection and for the differential diagnostic determination of leukemic cells in a sample of leucocytes, comprising treating the leucocytes with a supravital dye, the dye being a phthalein or sulphophthalein triphenylmethane dye and evaluating the resultant different staining of healthy and leukemic cells, the healthy cells remaining colorless, while the leukemic cells are stained.

2. A method of claim 1 wherein the dye is eosine, erythrosine, phloxine, bromophenol blue or bromochlorophenol blue.

3. A method of claim 1 wherein the concentration of the dye is 0.01 to 0.5% in an aqueous solution.

4. A method of claim 1 wherein the sample of leucocytes is a blood sample.

5. A method of claim 4 wherein the concentration of the dye is 0.01 to 0.5% in a physiological saline solution.

6. A method of claim 1 wherein the evaluation is performed using a microscope.

* * * * *